United States Patent [19]

Kelly et al.

[11] Patent Number: 5,767,314
[45] Date of Patent: *Jun. 16, 1998

[54] SELECTIVE ACYLATION OF MONOALKYLHYDRAZINES

[75] Inventors: Martha Jean Kelly, Norristown; Anne Marie Budenz, Sellersville, both of Pa.

[73] Assignee: Rohm and Haas Company, Phila, Pa.

[*] Notice: The term of this patent shall not extend beyond the expiration date of Pat. No. 5,675,037.

[21] Appl. No.: 125,969

[22] Filed: Sep. 23, 1993

Related U.S. Application Data

[63] Continuation-in-part of Ser. No. 628,770, Dec. 17, 1990, Pat. No. 5,675,037.

[51] Int. Cl.⁶ .................................................. C07C 243/10
[52] U.S. Cl. ........................... 564/149; 564/148; 564/150
[58] Field of Search ................................. 564/149, 150, 564/148; 514/614

[56] References Cited

U.S. PATENT DOCUMENTS

| | | | |
|---|---|---|---|
| 4,046,775 | 9/1977 | Bailey | 548/537 |
| 4,954,655 | 9/1990 | Kelly | 564/464 |
| 5,110,986 | 5/1992 | Kelly | 564/149 |
| 5,166,378 | 11/1992 | Kim et al. | 554/54 |

FOREIGN PATENT DOCUMENTS 347216  12/1989  European Pat. Off. .

OTHER PUBLICATIONS

Salim, et al., "1,1,1-Trichloropropane: A Mild Selective Acetylating Agent" *Synthetic Communications*, 19(7&8), 1181-1187 (1989).

Rebelo et al., "Use of 2,2,2-Trichloro-1-Arylethanones as Benzoylating Agents", *Synthetic Communications* 17(14), 1741-1748 (1987).

Zabricky, Jacob, *The Chemistry of Amides*, Interscience Publishers, A Division of John Wiley & Sons (1970).

*Primary Examiner*—Shailendra Kumar
*Attorney, Agent, or Firm*—Thomas D. Rogerson Patent Attorney

[57] ABSTRACT

A process for selectively monoacylating monoalkylhydrazines by reacting such with trichloromethyl aryl ketones.

25 Claims, No Drawings

SELECTIVE ACYLATION OF MONOALKYLHYDRAZINES

This application is a continuation-in-part of Ser. No. 07/628,770 filed on Dec. 17, 1990, now U.S. Pat. No. 5,675,037.

1-Acyl-2-alkylhydrazines, e. g. Acyl-N(—H)-N'(—H)—R, are useful intermediates in the process of preparing 2-alkyl-1,2-diacylhydrazines in which the diacyl moieties can have independently differing substituent groups on each acyl moiety. Such 2-alkyl-1,2-diacylhydrazines are known to have useful insecticidal activity.

The acylation of monoalkylhydrazines can be represented by the following reaction scheme (I):

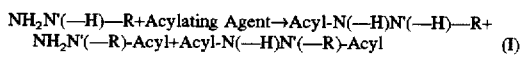

NH$_2$N'(—H)—R+Acylating Agent→Acyl-N(—H)N'(—H)—R+ NH$_2$N'(—R)-Acyl+Acyl-N(—H)N'(—R)-Acyl    (I)

"Acyl-" can alternatively be expressed as an arylcarbonyl, e.g. "Aryl-C(=O)—".

Selectivity problems are present in acylating monoalkylhydrazines since the hydrazinal moiety is a difunctional molecule, e.g. —NN'(R)—. There are two types of selectivity problems. One is the selectivity to monoacylate monoalkylhydrazine, e.g. Acyl-N(—H)N'HR or NH$_2$N'(—R)-Acyl, while preventing or minimizing diacylation, e.g. Acyl-N(—H)N'(—R)-Acyl. The other is control of the regioselectivity of acylation to selectively produce Acyl-N(—H)N'(—R)—H versus NH$_2$N'(—R)-Acyl.

Known reactions produce a mixture not having N-acyl-N'-alkylhydrazine in a relatively high proportion. Prior acylating agents include acid chlorides, anhydrides and esters, such as benzoyl chloride and acetyl chloride. In P. A. S. Smith, "Derivatives of Hydrazines and other Hydronitrogens having N-N Bonds", Benjamin/Cummings Publishing Company, Reading Mass., 1983, on pages 11 through 12 is described the reaction of methylhydrazine with acetyl chloride to produce N'-acetyl-N'-methylhydrazine, e.g.

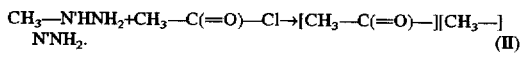

CH$_3$—N'HNH$_2$+CH$_3$—C(=O)—Cl→[CH$_3$—C(=O)—][CH$_3$—]N'NH$_2$.    (II)

There is also reported the reaction of acetic anhydride with methyl hydrazine to produce a mixture of NH$_2$N'(—CH$_3$)-Acyl and Acyl-N(-)HN'(—CH$_3$)H in a ratio of 38:1. The reaction of ethyl acetate and methylhydrazine is reported to produce an analogous product ratio of 1:3,3. In a third reaction, the reaction of tert-butylhydrazine with benzoyl chloride results in a product described as largely resulting in Benzoyl-NH-N'H-t-butyl.

The reactions of the prior art produce either N'-acyl-N'-alkylhydrazines or a mixture of products which require separation or some other recovery process for the desired N-acyl-N'-alkylhydrazine. What is needed is a process for the production of N-acyl-N'-alkylhydrazines in relatively high proportions to the other products possible from the reaction.

SUMMARY

This invention relates to a process for preparing monoacylated monoalkylhydrazines. More particularly, this invention relates to a process which comprises reacting a trichloromethyl aryl ketone with a monoalkylhydrazine to obtain selectively a desired N-monoacyl-N'-monoalkylhydrazine.

EMBODIMENTS OF THE INVENTION

This invention relates to a process for selectively preparing monoacylated hydrazines. More particularly, in one embodiment this invention relates to a process which comprises reacting a trichloromethyl aryl ketone and monoalkylhydrazine to obtain a N-monoacyl-N'-monoalkylhydrazine. Accordingly, the invention is a process for preparing an N-acyl-N'-alkylhydrazine which comprises reacting a monoalkylhydrazine, or the corresponding monoalkylhydrazine hydrate or monoalkylhydrazine salt, with a trichloromethyl aryl ketone. Preferably, the invention is a process comprising effectively reacting a monoalkylhydrazine, or the corresponding monoalkylhydrazine hydrate or monoalkylhydrazine salt, with a trichloromethyl aryl ketone to produce a reaction product comprising substantially N-acyl-N'-alkylhydrazine, more preferably essentially N-acyl-N'-alkylhydrazine.

The general reaction is shown in Equation (III):

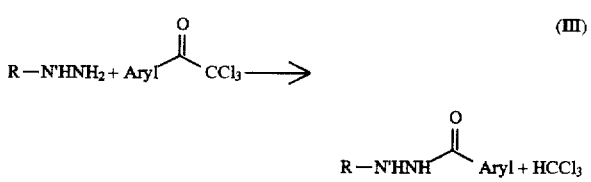

wherein

R is a straight or branched (C$_1$–C$_8$)alkyl, preferably branched (C$_4$–C$_6$) alkyl, more preferably neopentyl, methylneopentyl or tert-butyl, even more preferably tert-butyl; and Aryl is phenyl substituted with one to three substituents independently selected from hydrogen; bromide; chloride; fluoride; iodide; straight or branched (C$_1$–C$_6$)alkyl, preferably methyl, ethyl, propyl, and butyl; straight or branched (C$_1$–C$_6$)alkoxy, preferably methoxy; straight or branched halo(C$_1$–C$_6$)alkyl, preferably trifluoromethyl; and straight or branched halo(C$_1$–C$_6$)alkoxy, preferably trifluoromethoxy; or is naphthyl.

In a preferred embodiment, R is tert-butyl and Aryl is 4-(C$_1$–C$_6$)alkylphenyl, 2,3-di(C$_1$–C$_6$)alkylphenyl, 4-halophenyl, 2-(C$_1$–C$_6$)alkyl-3-(C$_1$–C$_6$)alkoxyphenyl, 2-(C$_1$–C$_6$)alkyl-3-halophenyl, 2,3-dihalophenyl, 2-halo-3-(C$_1$–C$_6$)alkylphenyl, 2,3-di(C$_1$–C$_6$)alkoxyphenyl, 2-halo-3-(C$_1$–C$_6$)alkoxyphenyl or 2,3,5-tri(C$_1$–C$_6$)alkylphenyl.

More preferably, Aryl is 4-ethylphenyl, 4-chlorophenyl, 2,3-dimethylphenyl, 2-methyl-3-methoxyphenyl, 4-methylphenyl, 4-n-propylphenyl, 2-methyl-3-chlorophenyl, 2,3-dimethoxyphenyl, 2-methyl-3-bromophenyl, 2-methyl-3-fluorophenyl, 2,3-dichlorophenyl, 2-fluoro-3-chlorophenyl, 2,3-difluorophenyl, 4-isopropylphenyl, 2-chloro-3-methylphenyl, 2-bromo-3-methylphenyl, 2-chloro-3-methoxyphenyl, 2-ethyl-3-chlorophenyl, 2-fluoro-3-methylphenyl or 2,3-dimethyl-5-isopropylphenyl.

The alkylhydrazine used in the process can be a hydrate, the neat alkylhydrazine, or a monoalkylhydrazine salt. Such salts are exemplified by alkylhydrazine hydrochloride, alkylhydrazine sulfate and alkylhydrazine hydrohalide. In the case where a monoalkylhydrazinal salt is used, an equivalent of base is added to the reaction to produce the alkylhydrazine. Examples of bases usable include potassium carbonate, sodium acetate, sodium methoxide, sodium ethoxide, triethylamine, and sodium hydroxide. A preferred base is sodium hydroxide or triethylamine.

In one embodiment the process for preparing the above monoacylmonoalkylhydrazine by reacting at a temperature between about 10° C. and 100° C. a monoalkylhydrazine with a trichloromethyl aryl ketone is performed under at least substantially, preferably essentially, anhydrous conditions. Such anhydrous conditions can be attained by reduction of the free water and/or water of hydration of one or more of the reactants prior to admixing or reacting. For example, one technique for such water reduction can be the treating of reactants and solvents using molecular sieves.

The proportions of trichloromethyl aryl ketone and monoalkylhydrazine reactants are preferably selected to provide a process comprising effectively reacting monoalkylhydrazine, or the corresponding hydrate or hydrazinal salt, with a trichloromethyl aryl ketone to produce a reaction product comprising substantially N-acyl-N'-alkylhydrazine, more preferably essentially monoacylhydrazine or N-acyl-N'-alkylhydrazine. The mole proportion of monoalkylhydrazine to trichloromethyl aryl ketone reactants should be approximately equimolar; that is, the mole proportion of monoalkylhydrazine:ketone can range preferably from about 0.75:1.0 to about 1.25:1.0; more preferably from about 0.9:1.0 to about 1.1:1.0.

The effective reaction produces a product comprising substantially N-acyl-N'-alkylhydrazine, more preferably essentially N-acyl-N'-alkylhydrazine. "Selectivity factor" relative to the reaction involving alkylhydrazine is defined herein as the mole ratio of (N-acyl-N'-alkylhydrazine)/ (N-acyl-N'-alkylhydrazine and N'-acyl-N'-alkylhydrazine and N,N'-diacyl-N'-alkylhydrazine) in the reaction product. The effective reaction preferably produces a product with a selectivity factor for the monoalkylhydrazine reaction of at least about 0.9, more preferably at least about 0.95, even more preferably at least about 0.99.

The reaction process can be carried out in a variety of solvents, such as methanol, ethanol, isopropanol, xylene, water, ethyl acetate, toluene, chloroform, hexane, triethylamine and methylene chloride. Preferred solvents are aprotic solvents, such as xylene, toluene, triethylamine and methylene chloride. Mixtures of solvents can be used, such as a methylene chloride and triethylamine mixture. Accordingly, the reaction process can be performed neat or in one or more solvents selected from a group consisting of methanol, ethanol, isopropanol, xylene, water, ethyl acetate, toluene, chloroform, hexane, triethylamine and methylene chloride. The reaction process is carried out preferably at atmospheric pressure, but need not be. The process is carried out at a temperature between about 10° C. and about 100° C., preferably between about 20° C. and about 50° C.

The following examples further illustrate the invention but are not intended to limit.

EXAMPLES

Example 1

1-(4-Ethylbenzoyl)-2-t-butylhydrazine using α,α,α-trichloro-4-ethylacetophenone in methylene chloride To a mixture of t-butylhydrazine hydrochloride (6.36 grams (g), 50 millimoles (mmol)) 5.3 g of water, 20 milliliters (ml) of methylene chloride and 4.0 g of 50% sodium hydroxide solution (50 mmol) under nitrogen, α,α,α-trichloro-4-ethylacetophenone (13.88 g, 95.2% purity, 52.5 mmol) is added dropwise at room temperature over 12 minutes. The reaction mixture is stirred at room temperature for 5.75 hours, then 0.4 g of additional sodium hydroxide solution is added and the reaction mixture is stirred overnight. The reaction then is quenched with water and the phases are separated. The methylene chloride phase is washed twice with water, dried over magnesium sulfate, filtered and evaporated in vacuo to yield 10.24 g (93% yield) of a pale yellow solid. This is found to contain 92.5% of 1-(4-ethylbenzoyl)-2-t-butylhydrazine, less than 0.3% of the isomer 1-(4-ethylbenzoyl)-1-t-butylhydrazine, and less than 0.3% of the 1,2-di(4-ethylbenzoyl)-1-t-butylhydrazine.

Example 2

1-(4-Chlorobenzoyl)-2-methylhydrazine using α,α,α-trichloro-4-chloroacetophenone in toluene To a mixture of methylhydrazine (1.63 g, 34.6 mmol) and 55 ml of toluene under nitrogen, α,α,α-trichloro-4-chloroacetophenone (8.55 g, 97.9% purity, 34.6 mmol) is added dropwise and the reaction mixture is stirred at room temperature for 2.75 hours. The resulting slurry then is filtered and the solids are washed with toluene and dried to yield 3.82 g (70% yield) of 1-(4-chlorobenzoyl)-2-methylhydrazine, mp 129.5°–131° C. (literature mp 132°–133° C., Meyer, R. F., J. Heterocyclic Chem., 1965, 2, 305).

Example 3

1-(4-Ethylbenzoyl)-2-t-butylhydrazine using α,α,α-trichloro-4-ethylacetophenone in methylene chloride/triethylamine To a 50 ml flask equipped with an overhead stirrer, thermometer and nitrogen is added 8.28 g (0.066 mol) of t-butylhydrazine hydrochloride. Triethylamine (6.58 g, 0.065 mol) and 15 ml of methylene chloride are added, both the triethylamine and the methylene chloride being previously dried over 3A molecular sieves. The mixture is stirred one hour, then 15.10 g (0.060 mol) of α,α,α-trichloro-4-ethylacetophenone are added over 45 minutes. The reaction temperature may be allowed to vary from room temperature to 40° C. during the feed. The reaction mixture is held three hours, then quenched by the addition of 15 ml of water and 5 ml of methylene chloride. The phases are separated. The organic phase is washed twice with water and 2 Normal sodium hydroxide solution, washed once with brine and stripped to yield 12.78 g off-white solids. The yield is 97% by weight of 1-(4-ethylbenzoyl)-2-t-butylhydrazine based on the trichloroketone. The purity is analyzed as 100% by HPLC. None of the isomer 1-(4-ethyl)benzoyl-1-t-butylhydrazine and none of the diacylated impurity 1,2-di(4-ethylbenzoyl)-1-t-butylhydrazine are detected at a limit of detection of 0.1%.

It should be understood that the instant specification and examples are set forth by way of illustration and not limitation, and various modifications and changes may be made without departing from the spirit and scope of the present invention as defined by the appended claims.

What is claimed is:

1. A process for preparing a monoacylmonoalkylhydrazine of the formula

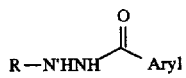

which comprises reacting at a temperature between about 10° C. and about 100° C. a monoalkylhydrazine of the formula NH$_2$N'(R)H or the corresponding hydrate or monoalkylhydrazinal salt with a trichloromethyl aryl ketone of the formula

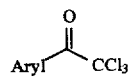

wherein

R is straight or branched (C$_1$–C$_8$)alkyl; and

Aryl is phenyl substituted with one to three substituents independently selected from hydrogen; bromide; chloride; fluoride; iodide; straight or branched (C$_1$–C$_6$)

alkyl; straight or branched ($C_1$–$C_6$)alkoxy; straight or branched halo($C_1$–$C_6$)alkyl; and straight or branched halo($C_1$–$C_6$)alkoxy; or is naphthyl.

2. The process of claim 1 which is carried out in an aprotic solvent.

3. The process of claim 1 wherein R is t-butyl.

4. The process of claim 1 wherein R is methyl.

5. The process of claim 1 wherein Aryl is 4-($C_1$–$C_6$)alkylphenyl.

6. The process of claim 5 wherein Aryl is 4-ethylphenyl.

7. The process of claim 1 wherein Aryl is 2,3-di($C_1$–$C_6$)alkylphenyl.

8. The process of claim 1 wherein Aryl is 2-($C_1$–$C_6$)alkyl-3-($C_1$–$C_6$)alkoxyphenyl.

9. The process of claim 8 wherein Aryl is 2-methyl-3-methoxyphenyl.

10. The process of claim 1 wherein Aryl is 2,3-dihalophenyl.

11. The process of claim 1 wherein Aryl is 2,3-di($C_1$–$C_6$)alkoxyphenyl.

12. The process of claim 1 wherein Aryl is 4-halophenyl.

13. The process of claim 12 wherein Aryl is 4-chlorophenyl.

14. The process of claim 1 wherein Aryl is 2-($C_1$–$C_6$)alkyl-3-halophenyl.

15. The process of claim 1 wherein Aryl is 2-halo-3-($C_1$–$C_6$)alkylphenyl.

16. The process of claim 1 wherein Aryl is 2-halo-3-($C_1$–$C_6$)alkoxyphenyl.

17. The process of claim 1 wherein Aryl is 2,3,5-tri($C_1$–$C_6$)alkylphenyl.

18. The process of claim 1 which is carried out at a temperature between about 20° C. and about 50° C.

19. The process of claim 1 carried out under at least substantially anhydrous conditions.

20. A process comprising effectively reacting a monoalkylhydrazine, or the corresponding monoalkylhydrazine hydrate or monoalkylhydrazine salt, with a trichloromethyl aryl ketone to produce a reaction product comprising substantially N-acyl-N'-alkylhydrazine.

21. The process of claim 20 wherein said reaction product comprises essentially N-acyl-N'-alkylhydrazine.

22. A process comprising effectively reacting a monoalkylhydrazine, or the corresponding monoalkylhydrazine hydrate or monoalkylhydrazine salt, with about an equimolar amount of trichloromethyl aryl ketone to produce a N-acyl-N'-alkylhydrazine reaction product with a selectivity factor of at least about 0.9.

23. The process of claim 22 wherein the selectivity factor is at least about 0.95.

24. The process of claim 23 wherein the selectivity factor is at least about 0.99.

25. The process of claim 22 wherein the proportion of monoalkylhydrazine to ketone ranges from about 0.9:1.0 to about 1.1:1.0.

* * * * *